US009333057B2

(12) United States Patent
Benzon

(10) Patent No.: US 9,333,057 B2
(45) Date of Patent: May 10, 2016

(54) SCREW CHANNEL DIRECTING DEVICE FOR A DENTAL SUPERSTRUCTURE AND METHODS FOR MANUFACTURING A DENTAL SUPERSTRUCTURE

(71) Applicant: Heraeus Dental AB, Helsingborg (SE)

(72) Inventor: Sture Benzon, Hoganas (SE)

(73) Assignee: Heraeus Kulzer Nordic AB, Helsingborg (SE)

( * ) Notice: Subject to any disclaimer, the term of this patent is extended or adjusted under 35 U.S.C. 154(b) by 0 days.

(21) Appl. No.: 13/935,673

(22) Filed: Jul. 5, 2013

(65) Prior Publication Data
US 2014/0065574 A1    Mar. 6, 2014

(30) Foreign Application Priority Data

Jul. 11, 2012    (SE) .................................... 1250814

(51) Int. Cl.
*A61C 8/00*        (2006.01)
*A61C 13/00*       (2006.01)
*A61C 9/00*        (2006.01)
*A61C 13/34*       (2006.01)

(52) U.S. Cl.
CPC ............. *A61C 8/0089* (2013.01); *A61C 8/0053* (2013.01); *A61C 8/0068* (2013.01); *A61C 9/0006* (2013.01); *A61C 13/0004* (2013.01); *A61C 13/0006* (2013.01); *A61C 13/34* (2013.01)

(58) Field of Classification Search
CPC .... A61C 8/005; A61C 8/0054; A61C 8/0059; A61C 8/0066; A61C 8/0078; A61C 8/0053; A61C 13/34; A61C 8/0089; A61C 8/0068; A61C 9/0006; A61C 13/0006
USPC ....................................... 433/171–176, 201.1
See application file for complete search history.

(56) References Cited

U.S. PATENT DOCUMENTS 5,133,662 A * 7/1992 Metcalfe ....................... 433/169

FOREIGN PATENT DOCUMENTS

| EP | 1 547 543 | 6/2005 | |
| WO | WO 9004951 A1 * | 5/1990 | ............ A61C 8/0048 |
| WO | WO 9203984 A1 * | 3/1992 | ............. A61C 8/005 |

* cited by examiner

*Primary Examiner* — Cris L. Rodriguez
*Assistant Examiner* — Mirayda A Aponte
(74) *Attorney, Agent, or Firm* — Merchant & Gould P.C.

(57) ABSTRACT

A screw channel directing device for a dental superstructure includes a screw channel part and an implant cooperating part, the former having a screw member seat with an elongated screw hole in the proximal end. The proximal end of the screw channel part is bowl shaped, having a convex outer bottom. The implant cooperating part comprises a collar-shaped lower implant cooperating part to be connected to a dental implant and a collar-shaped upper implant cooperating part. The lower implant cooperating part and said upper implant cooperating part form a first ball joint. The upper implant cooperating part has a distal concave seat with a radius corresponding to the radius of the outer bottom surface of the screw channel part to form a second ball joint.

7 Claims, 5 Drawing Sheets

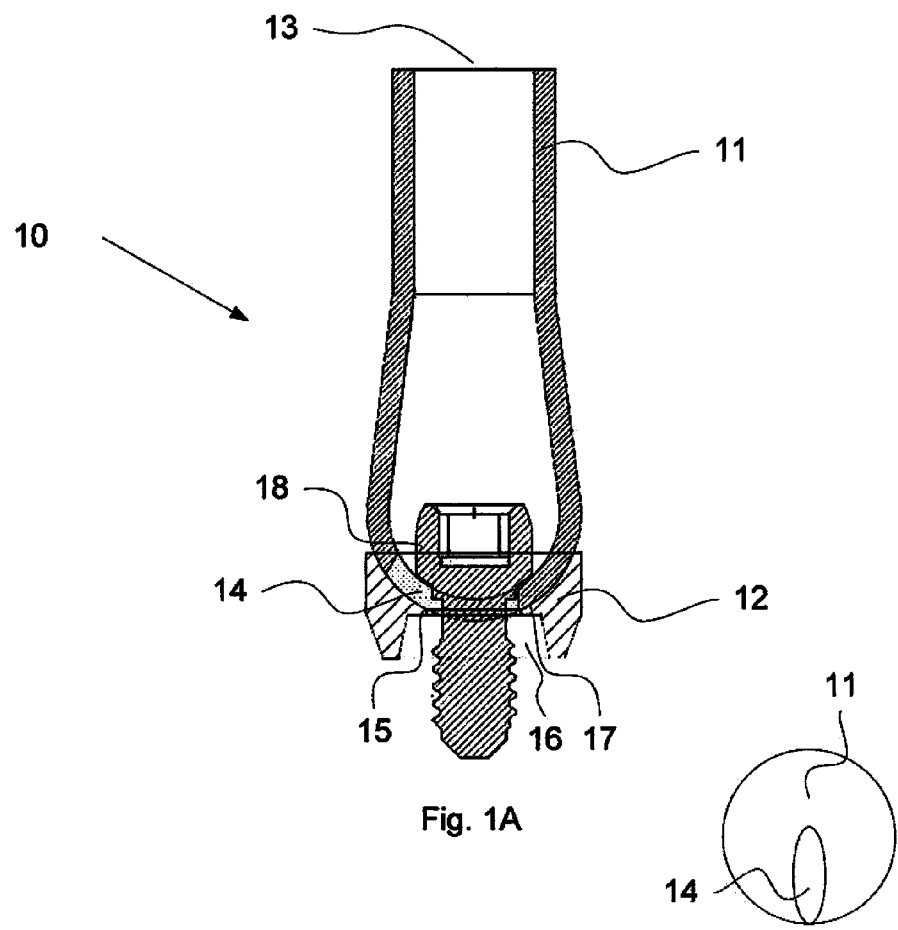
Fig. 1A
Fig. 1B
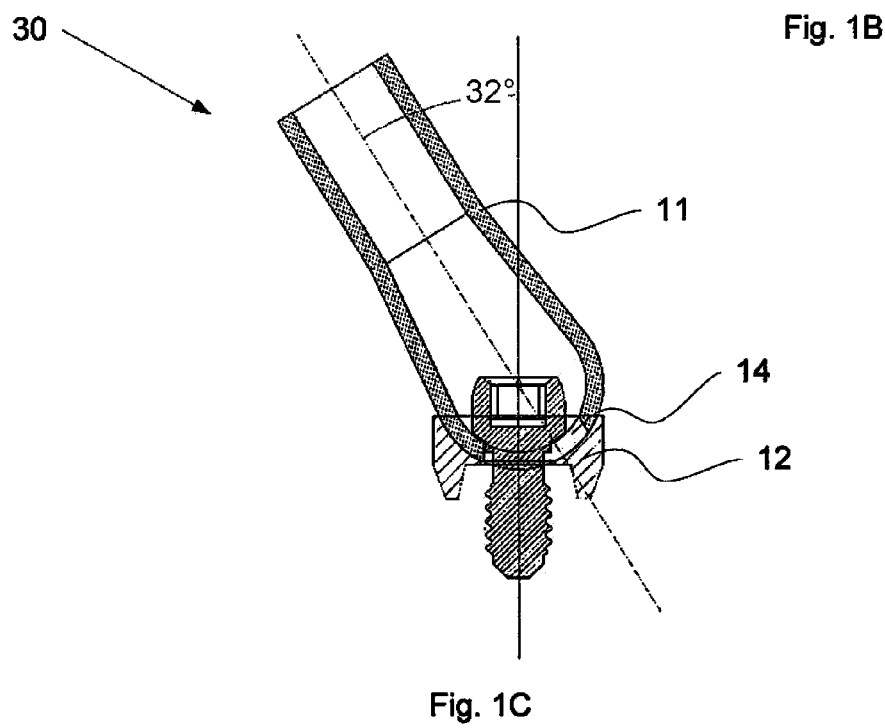
Fig. 1C

SCREW CHANNEL DIRECTING DEVICE FOR A DENTAL SUPERSTRUCTURE AND METHODS FOR MANUFACTURING A DENTAL SUPERSTRUCTURE

This application claims benefit of Serial No. 1250814-9, filed 11 Jul. 2012 in Sweden and which application is incorporated herein by reference. To the extent appropriate, a claim of priority is made to the above disclosed application.

TECHNICAL FIELD

The present invention relates to a screw channel directing device for a dental superstructure for attachment to dental implants or dental abutments. The present invention also relates to methods for manufacturing such dental superstructures through casting or CAD/CAM milling/sintering with angled screw channels for screw retaining said superstructure to the dental implant or dental abutment.

BACKGROUND

When securing a dental prosthesis to the jaw of a patient, it is commonly known to attach a superstructure to osseointegrated dental implants. However, since the position and angle of the dental implants vary greatly from patient to patient, the use of angled distances is common These distances are placed upon the dental implant, and the superstructure is then most often cemented to the distances, since it is difficult to screw retain the superstructure to such distances. However, when using separate distances, these will inevitably extend—at least to some extent—in the axial direction of the dental implant. It is then often very difficult or even impossible to apply the superstructure on such distances, since the application of the superstructure calls for a substantially parallel arrangement of the distances. Also, the mounting process when using such distances is very complicated and cumbersome, since a vast number of different distances must be tested on the implants, to find the needed match. Also, interfaces between the distances and the superstructure are hygienically bad.

In order to model the desired position of the screw channel mouth in screw retained superstructures, it is known to position acrylic tubes on a model of the jaw of a subject. The model shows the position of the osseointegrated dental implants, and the acrylic tubes are placed at these positions and bent to the desired curvature before a mould is formed, based on the bent acrylic tubes. Subsequently, separate seat support cylinders are planarized together with the casted superstructure, whereafter the separate screw member seat support cylinders are welded onto the casted superstructure.

However, it may be hard to bend the acrylic tubes correctly. Bending the tubes to the desired curvature is tedious and the tubes may flex after bending, which may result in a mould with erroneous angles. Furthermore, it is only possible to obtain bent screw channels, following a curvature, whereby the angle between the central axis of the mouth of the attached screw seat and the central axis of the screw channel mouth is limited to angles less than 17 degrees.

Several screw channel directing devices for use in dental superstructures have been designed, but they may all suffer from certain different disadvantages. There is thus a need for an improved screw channel directing device, at least for demanding uses.

SUMMARY OF THE INVENTION

The above and other objects are according to the invention fulfilled by a screw channel directing device for a dental superstructure, comprising a screw channel part and an implant cooperating part, said screw channel part comprising a screw member seat with a screw hole in the proximal end, wherein the proximal end of the screw channel part is bowl shaped, such that the inner bottom surface has a concave shape and its outer bottom surface has a convex shape, and wherein the screw hole of the screw member seat is a long hole, and wherein said implant cooperating part comprises a collar-shaped lower implant cooperating part to be connected to a dental implant and a collar-shaped upper implant cooperating part, said lower implant cooperating part having a distal concave seat and said upper implant cooperating part having a proximal convex bottom surface with a radius corresponding to the radius of the concave seat of the lower implant cooperating part to form a first ball joint and said upper implant cooperating part having a distal concave seat with a radius corresponding to the radius of the outer bottom surface of the screw channel part to form a second ball joint, the two ball joints having the effect that the screw channel part may be tilted/angled and transferred sideways in relation to a central axis of the lower implant cooperation part.

The invention also relates to a method for manufacturing a dental superstructure or part thereof, comprising the steps of
 (i) making a dental imprint from the mouth of a subject;
 (ii) mounting an analog in the imprint to obtain a working model;
 (iii) attaching a screw channel directing device, comprising a screw channel part and an implant cooperating part comprising a lower implant cooperating part and an upper implant cooperating part, said screw channel part being tiltable in relation to the implant cooperating part, to the working model;
 (iv) tilting the screw channel part in relation to the implant cooperating part into a desired angle;
 (v) shaping a mold creating a master superstructure or part thereof onto the screw channel directing device;
 (vi) forming a mold based on the master superstructure or part thereof; and
 (vii) casting or CAD/CAM shaping the dental superstructure or part thereof.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIG. 1 is a schematic cross-section of a tiltable screw channel directing device according to an embodiment.

DESCRIPTION OF EMBODIMENTS

Figure 2A:
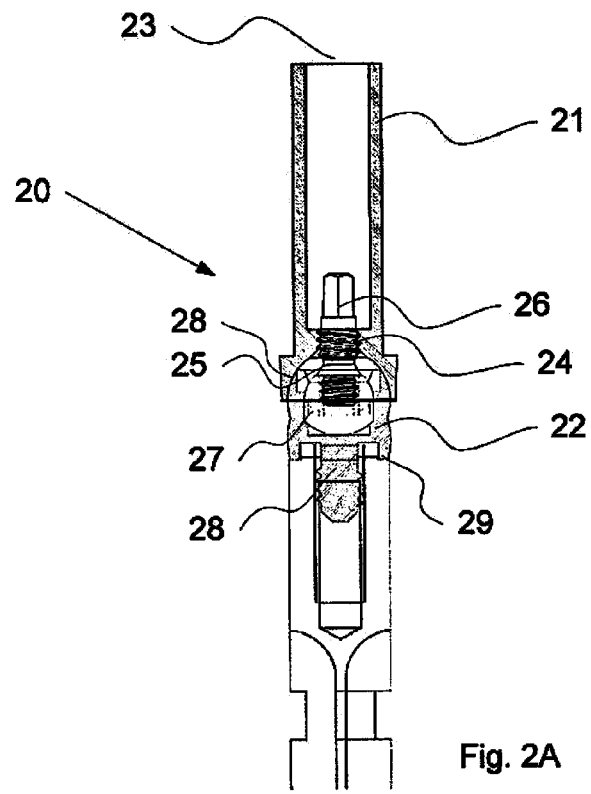
FIG. 2 is a schematic cross-section of a tiltable screw channel directing device according to another embodiment

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Embodiments of the present invention relate to methods for producing a cast dental superstructure, with improved angling possibilities and facilitated manufacturing. The embodiments are realized by the aid of an angled distance in form of a screw channel directing device. The screw channel directing device is used to obtain an angled screw channel in the cast dental superstructure, whereby the angle between a central axis of a screw channel mouth and the central axis of the dental implant, osseointegrated in the jaw of a subject, may be increased, in comparison with cast superstructures with bent screw channels according to the prior art.

In an embodiment according to FIG. 1, a screw channel directing device 10 is provided. The screw channel directing device 10 comprises a screw channel part 11 and an implant cooperating part 12. The screw channel part 11 comprises a screw channel mouth 13 in the distal end. The screw channel part 11 also comprises a screw member seat 14 in the proximal end of the screw channel. The screw channel part 11 may be substantially cylindrical with a central axis and a distal screw channel mouth end and a proximal screw member seat end. The central axis of the screw channel runs through the center of the screw channel mouth and through the mouth of the screw member seat 14. Preferably, the screw channel part 11 has a circular cross-section along the central axis of the screw channel. The circular cross-section may have a first diameter at the distal end, and then increasing when moving along the longitudinal central axis of the screw channel towards its proximal end. In the proximal end, the screw channel part 11 is bowl shaped, such that the inner bottom surface has a concave shape and its outer bottom surface 15, i.e. its proximal end, has a convex shape. The screw hole of the screw member seat 14 is a long hole. A long hole is a stretched hole.

The implant cooperating part 12 is a collar comprising an implant seat 16 at its proximal end, and a distal concave screw channel part seat 17. The screw channel part seat 17 has a radius corresponding to the radius of the outer proximal end of the screw channel part 11, such that the screw channel part 11 may be tilted angled in relation to the implant onto which the implant cooperating part 12 is arranged. The implant seat 16 at the proximal end of the implant cooperating part 12 may be adjusted according to different implant systems available on the market, such that different implant cooperating parts may be used depending on which dental implant is inserted into the jaw bone of the patient.

When angling/tilting the screw channel part 11 on the implant cooperating part 12, a screw member 18 is inserted into the screw channel of the screw channel part 11. Then the screw channel part 11 is loosely screwed into the dental implant through the lumen of the collar of the implant cooperating part 12, with the implant cooperating part 12 distally of the implant but proximally of the screw channel part 11. In this position the screw channel part 11 may be angled/tilted into desired position, by rotating the screw channel part 11 such that the long hole gets into the desired position, i.e. in which the long hole is in the direction of the plane in which the screw channel part 11 is wished to be angled/tilted. The long hole of the screw member part 11 may extend from the central axis towards the perimeter of the screw channel part 11, as can be seen in FIG. 1B, which shows the screw channel part 11 from the end which is intended to be positioned towards the working model. Thus, by sliding the screw channel part 11 in the concave screw channel part seat 17 of the implant cooperating part 12 along the extension of the long hole, when the implant cooperating part 12 is attached to the model, via the implant analog, but not yet fully secured, it is possible to tilt the hollow screw channel part 11 in relation to the model, as can be seen in FIG. 1C.

Figure 2B:
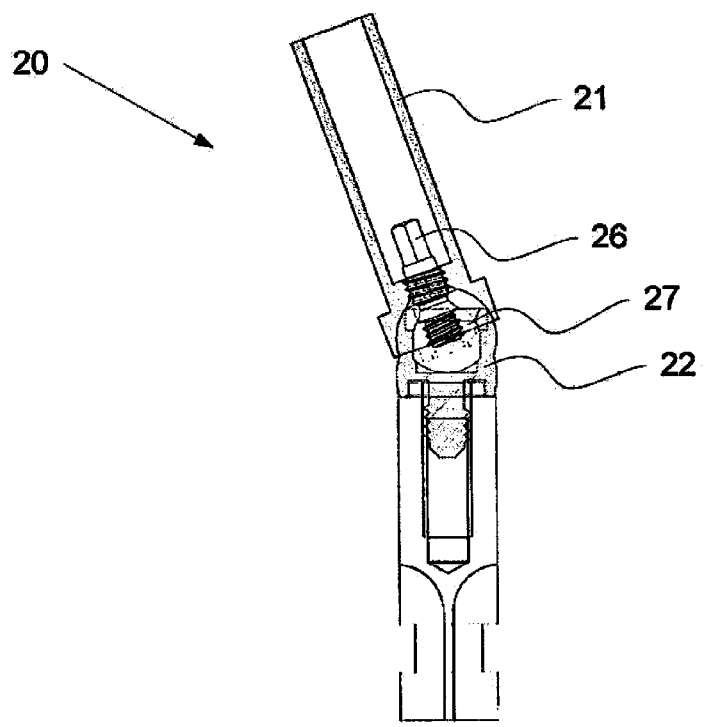

In FIG. 2 another embodiment of a screw channel directing device is illustrated. In this embodiment the screw channel directing device 20 comprises a screw channel part 21 and an implant cooperating part 22. The screw channel part 21 comprises a screw channel mouth 23 in the distal end. The screw channel part 21 may be substantially cylindrical along the extension of the screw channel, with a central axis and a distal screw channel mouth end and a proximal screw hole 24 with an internal thread. The central axis of the screw channel is also the central axis of the screw channel mouth 23. Preferably, the screw channel part 21 has a circular cross-section along the central axis of the screw channel.

In the proximal end of the screw channel of the screw channel part 21 a screw member 25 is arranged. The screw member 25 extends through a screw member seat at the bottom proximal end of the screw channel of the screw channel part 21. The screw member 25 has a distal gripping portion 26 adapted for cooperation with a screwing device, such as screw driver, wrench, spanner, etc. In the proximal end the screw member has a screw member head 27. The screw member head 27 has head configuration in form of a peripheral contour, adapted for cooperation with the implant cooperating part 22 for screwing the implant cooperating part 22 into the dental implant or implant analog, in accordance with below. Proximally of the screw member seat, the screw channel part 21 comprises a concave interaction surface 28, for cooperation with the implant cooperating part 22.

In one embodiment, the screw member 25 has a right handed threaded part proximally of the gripping portion. This right handed threaded part may be used to screw the screw member distally, by rotating the distal gripping portion in a right handed way, to secure the implant cooperating part 22 to the dental implant or implant analog.

In another embodiment, the screw member 25 comprises two thread portions proximally of the distal gripping portion, in form of a distal thread portion and a proximal thread portion. Preferably, the distal screw portion is right-handed threaded while the proximal thread portion is left-handed threaded. The screw member head 27 is then attached to the screw member 25 via the proximal left-handed thread. When the screw member head 27 is connected to the screw member 25 via a left-handed thread, the screw member head 27 may be screwingly separated from the screw member 25, by rotating the gripping portion 26 in a left-handed way, once the screw member head is in a bottom position, i.e. either in bottom cooperation with the implant cooperation part 22 or when the implant cooperating part 22 and the screw channel part 21 are pressed against each other, in accordance with below. This brings about the technical effects of enabling separation of the screw channel part 21 and the implant cooperating part 22 when the screw channel part 21 is secured, such as welded, cast, or solded to the superstructure.

The implant cooperating part 22 has a proximal pin 28 with a threaded part, with an external thread, suitable for securing the implant cooperating part 22 to a dental implant. A dental implant seat cooperating part may be arranged at the distal end of the pin 28, by arranging a flange 29 circumferentially of the implant seat, said flange having an inner contour corresponding to the dental implant seat at the distal end of the dental implant. In accordance with above, different implant systems available on the market with differing implant seats, such that different implant cooperating parts 22 may be used depending on which dental implant is inserted into the jaw bone of the patient.

The implant cooperating part 22 has an inner gripping cavity in its distal end, said cavity corresponding in shape to the proximal screw member head of the screw member, such that the implant cooperating part 22 may be screwingly secured to the dental implant by screwing the implant cooperating part 22 into the dental implant with by rotating the screw member when the screw member head is in engaged cooperation with the distal inner gripping cavity of the implant cooperating part 22.

The implant cooperating part 22 has an outer convex shape, forming a convex interaction surface for cooperation with the screw channel part 21. The convex interaction surface is adapted to cooperate with the proximal concave proximal concave interaction surface of the screw channel part 21, such that the cooperation works as a ball joint, whereby the screw channel part 21 may be angled/tilted into the desired position.

The screw member head 27 is adapted to be inserted into the bottom of the cavity with the corresponding shape in the distal end of the implant cooperating part 22 when the screw channel part 21 is arranged in perfect alignment with the implant cooperating part 22, i.e. when the central axis of the screw channel part 21 coincides with the central axis of the implant cooperating part. When then the central axis of the screw channel part 21 is angled in relation to the central axis of the implant cooperating part 22, the screw member head 27 can no longer be separated from the implant cooperating part 22. This can be accomplished by having a slanting contact surface on the distal end of the screw member head 27, such as for example semi-spherical or spherical shape, and a corresponding negative slanting surface in the cavity of the implant cooperating part 22. In this way the screw member head 27 may be screwed distally to secure the screw channel part 21 to the implant cooperating part 22.

Figure 3:
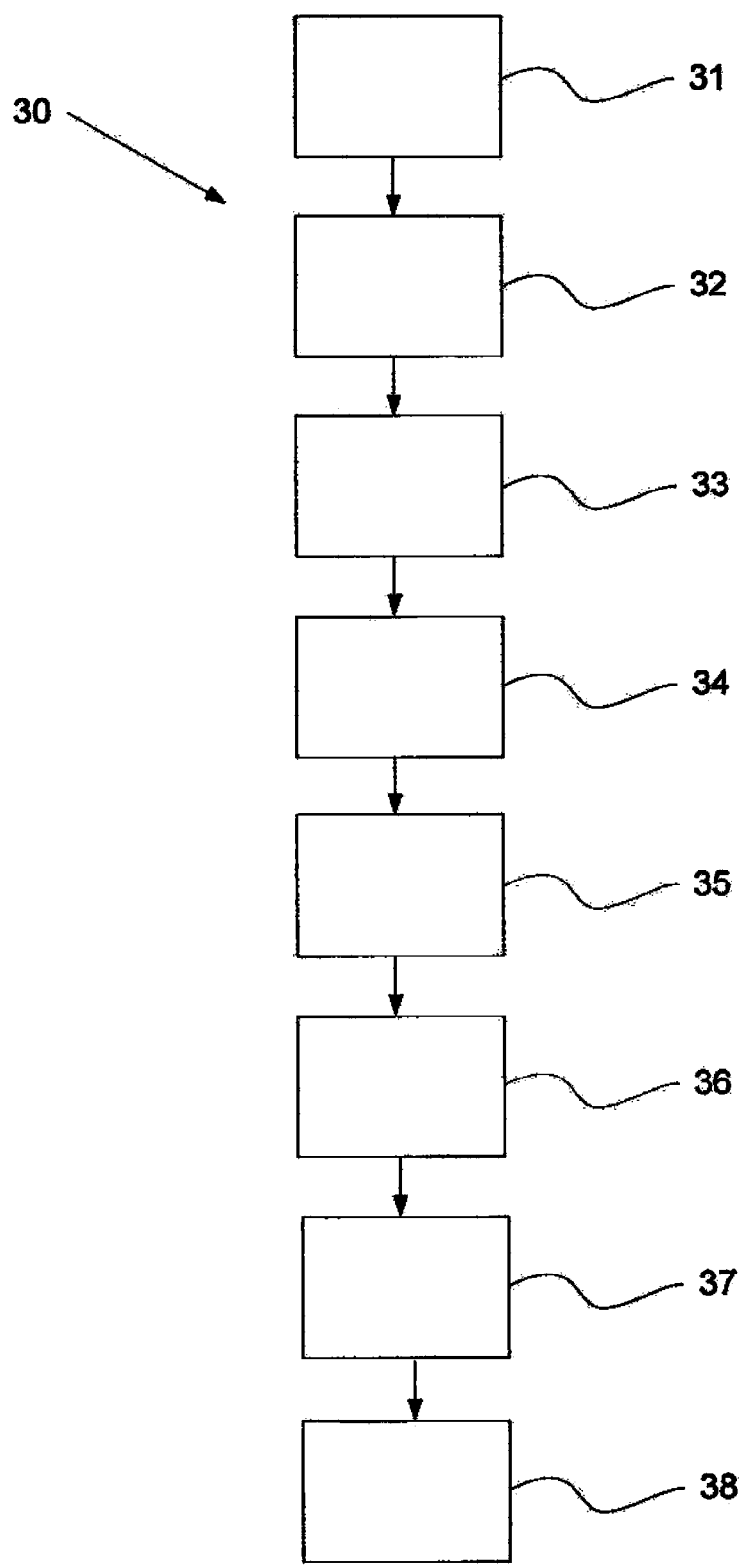
FIG. 3 is a flowchart showing the steps of a method according to an embodiment.

In an embodiment, according to the flow chart in FIG. 3, a method 30 for producing a cast dental superstructure is provided. The cast dental superstructure is manufactured by the aid of an angled distance, by means of screw channel directing devices according to above. The screw channel directing device is used to obtain an angled screw channel in the cast dental superstructure, whereby the angle between a central axis of a screw channel mouth and the central axis of the dental implant, osseointegrated in the jaw of a subject, may be increased, in comparison with cast superstructures with bent screw channels according to the prior art. Thus, the screw channel of the screw channel directing device has substantially one central axis extending through the hollow cylinder screw channel.

The screw channel directing device is tiltable due to a screw channel part and an implant cooperating part which are described above.

In one embodiment the screw channel part may be meltable in the casting temperature, such that the screw channel part disintegrates during casting. In these instances the screw channel part may be made of a plastics or wax.

A dental imprint is made 31 from a subject according to methods known to a person skilled in the art. From the imprint a model of the subjects dental situation is manufactured, according to methods known to the person skilled in the art. In the obtained model of the subjects dental situation an implant analog is mounted 32.

Then, a screw channel directing device, according to below, is attached 33 on the analog in the working model, with a laboratory screw. The angle of the screw channel directing device is adjusted by tilting 34 the screw channel part in relation to an implant cooperation part, comprised in the screw channel directing device. Then the laboratory screw is fastened to finally secure 35 the screw channel part of the screw channel directing device to the working model in a desired angle.

This is advantageous, since it is possible to achieve angles larger than 17 degrees, such as between 18 and 25, which is desirable since it allows for greater freedom in screw channel mouth placement on the superstructure. The angled screw channel, in contrast to the bent screw channel according to prior art cast superstructures, also improves access to the screw channel.

On top of the distance model, a superstructure master is made 36 from wax or another meltable material. Thus, a superstructure master has been obtained with an angled screw channel, wherein the angle has been optimally adapted in relation to the dental situation of the subject.

Thereafter, the master superstructure is dissembled by removing the laboratory screw, if the screw channel directing device according to FIG. 1 is used, or loosening the threaded pin of the implant cooperating part 22 from the implant analog, if the screw channel directing device according to FIG. 2 is used. The master superstructure may then be separated from the screw channel directing device by gently extracting the screw channel directing devices from the master superstructure.

It is also possible to leave the screw channel directing device in the master supertstructure.

In yet another embodiment, the master superstructure is scanned when being positioned on the screw channel directing device 10, 20, for subsequent CAD/CAM shaping, such as milling and sintering.

Then, the master superstructure is embedded in a cuvette with an embedding paste, specific for the material which ultimately will be used to cast the distance, which is appreciated by a person skilled in the art.

The cavity obtained when extracting the screw channel directing device or the screw channel of the screw channel directing device is also filled with embedding paste. In those instances in which the screw channel part of the screw channel directing device is of a material that melts during the casting procedure, in accordance with above, the molt in the subsequent casting will replace the screw channel part.

The cuvette is pre-heated according to the instructions specific for the embedding paste, which will make both the master superstructure and screw channel directing device melt, in those instances a screw channel directing device is made of a material that melts during this preheating, and the embedding paste hardens, forming 37 a mould.

Since the cavity of the screw channel directing device was also filled with embedding paste, the mold represents the geometrical inverse of a tubular, angular geometrical figure, i.e. the desired shape of the superstructure with angled screw channel.

The superstructure with angled screw channel is then cast 38 in a metal of choice, such as Titanium or Cobalt/Chromium alloy well known to a person skilled in the art, according to the recommendations of the manufacturer of the material. After cooling, the cast superstructure with angled screw channel may be blasted to create a smooth surface, preferably with aluminum oxide particles with a size between 110 and 250 μm.

Optionally, the metal surfaces, which are intended to interact with an analog/fixture, can be adjusted with a reamer. The other surfaces may be adjusted by means of a hard metal cutter.

The superstructure with angled screw channel is then ready to be fitted to the subject. The dental facing of the superstructure may be added according to methods known to a person skilled in the art.

Figure 4:
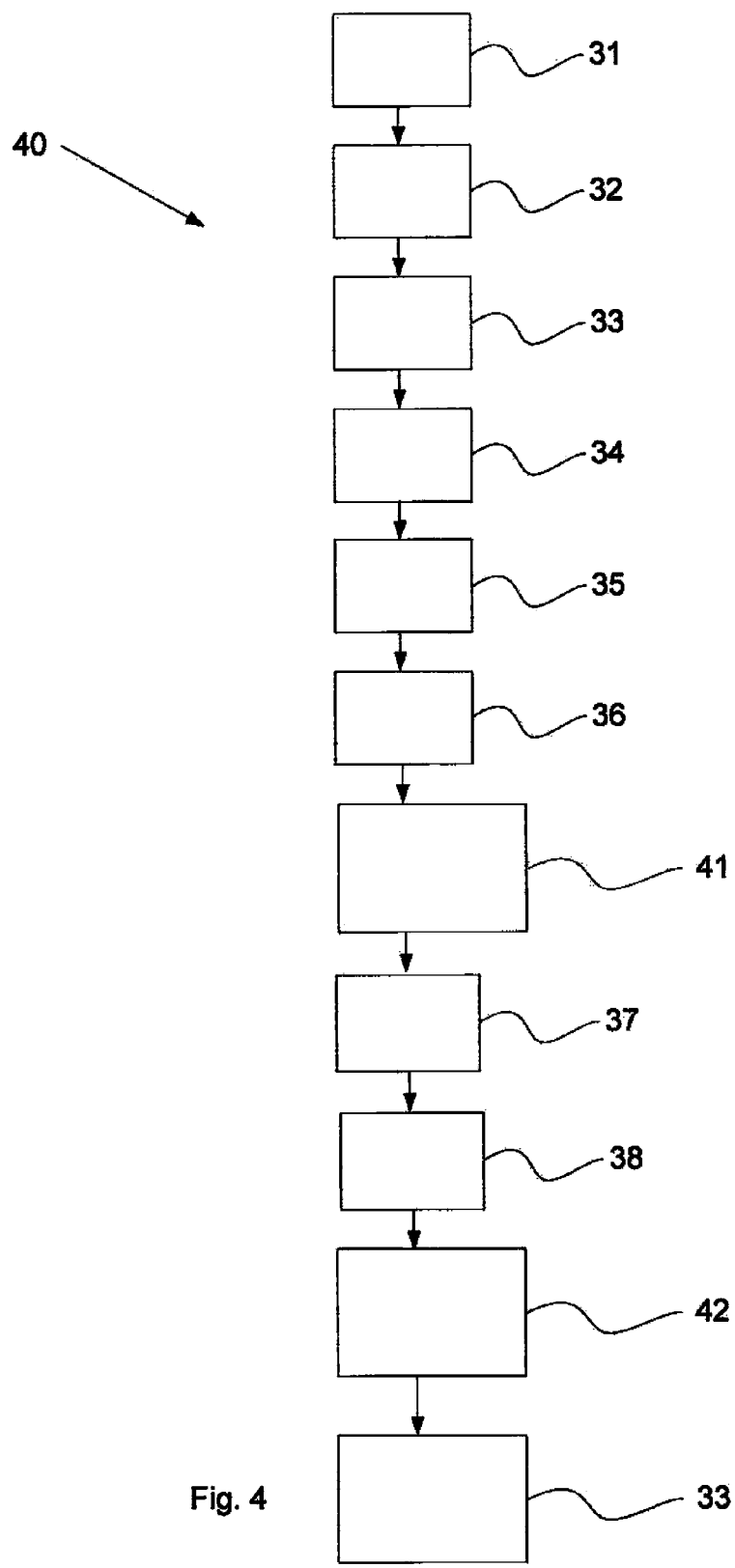
FIG. 4 is a flowchart showing the steps of a method according to another embodiment.

In another embodiment according to FIG. 4, a method 40 for producing a superstructure with angled screw channel, by means of a screw channel directing device with oversized screw channel part is provided.

The screw channel directing device is tiltable due to a screw channel part and an implant cooperating part, according to above.

The oversized screw channel part is larger than a subsequently used screw channel part, for reasons which will be apparent below.

The first steps of the method 40 are analogous to the previously described method 30.

A dental imprint is made 31 from a subject according to methods known to a person skilled in the art. An implant analog is mounted 32 in the imprint and a working model is made from plaster. An oversized screw channel part is attached 33 on the working model by means of the implant cooperation part, with a laboratory screw.

The angle of the screw channel directing device is adjusted by tilting 34 the screw channel part in relation to the implant cooperation part before the laboratory screw is fastened to finally secure 35 the tiltable, oversized distance model part to the working model, in a desired angle.

Optionally, the distance model is wax isolated to create a smooth surface.

On top of the distance model, a master superstructure is made 36 from a meltable material, such as the plastic or wax as described above.

Optionally, a pre-casting is made.

The master superstructure is removed 41 from the oversized screw channel part in an occlusional direction, after the master superstructure has been detached from the implant analog(s).

The master superstructure is then embedded in a cuvette with an embedding paste, specific for the material which ultimately will be used to cast the distance as is appreciated by a person skilled in the art.

The cuvette is pre-heated according to the instructions specific for the embedding paste, which will make the construct melt and the embedding paste harden, forming 37 a mould.

A superstructure is cast 38 in the mould with the metal of choice, such as Titanium or Cobalt/Chromium alloy well known to a person skilled in the art, according to the recommendations of the manufacturer. The cast superstructure with angled screw channel is blasted to create a smooth surface, preferably with aluminum oxide particles with a size between 110 and 250 μm.

Optionally, the metal surfaces which are intended to interact with an analog/fixture can be adjusted with a reamer. The other surfaces may be adjusted by means of a hard metal cutter.

A screw channel directing device 11, 21 is then inserted into the cavities formed by the oversized screw channel parts. The size of the screw channel directing device 11, 21 is thus adapted to fit in the formed/cast cavity. The superstructure is then fastened to a working model by laboratory screw(s).

The screw channel directing device are then fixed to the master superstructure 42, such as welded, glued or soldered, together. This may be done by first welding/gluing/soldering the screw channel directing device to the cast superstructure occlusionally and then at the position of the implant cooperating part, thus forming a superstructure with angled screw channel(s).

Next, the screw channel directing device is cut 43 to fit with the cast superstructure, so that no part extends outside the edges of the superstructure occlusally. The superstructure is then ready to be fitted to the subject. The dental facing of the superstructure may be added according to methods known to a person skilled in the art.

The screw channel part 11, 21 may be made of a material that melts during production of the angled distance which the model is designed to precede. Examples of meltable materials are plastic or wax.

The screw channel part 11, 21 of the screw channel directing device 10, 20 may alternately be made from a metal, such as Titanium or a Cobalt/Chromium alloy.

Figure 5:
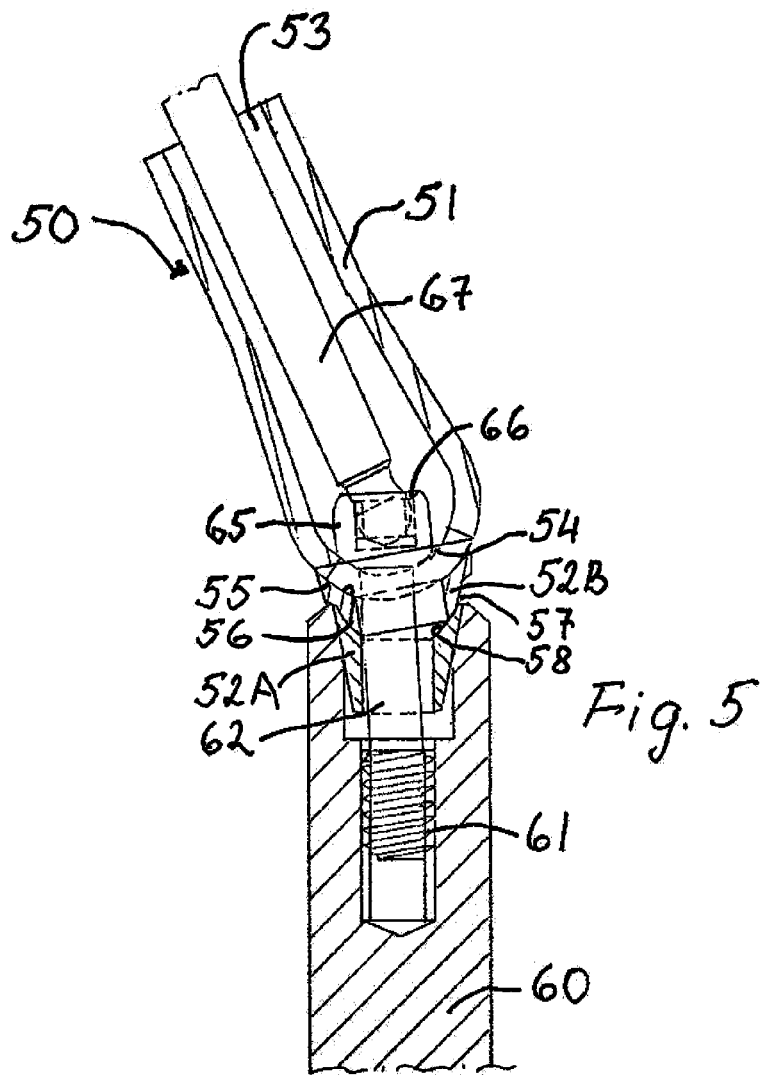
FIG. 5 is a schematic cross-section of a tiltable screw channel directing device according to a further embodiment.

FIG. 5 shows a further embodiment of a screw channel directing device 50 having certain similarities with the embodiment of FIG. 1. Also in this further embodiment the screw channel directing device 50 comprises a screw channel part 51 and an implant cooperating part 52, which—as will be described in more detail below—comprises a lower implant cooperating part 52A and an upper implant cooperating part 52B movable in relation to each other.

The screw channel part 51 has a screw channel mouth 53 in the distal end and a screw member seat 54 in the proximal end. It may be substantially cylindrical with a central axis, which runs through the center of the screw channel mouth 53 and through the mouth of the screw member seat 54. Preferably, the screw channel part 51 has a circular cross-section along its central axis. The screw channel part 51 may have an increasing diameter from its distal end towards its proximal end. In its proximal end, the screw channel part 51 is bowl shaped, such that the inner bottom surface has a concave shape and its outer bottom surface 55, i.e. its proximal end, has a convex shape. The screw hole of the screw member seat 54 is a long hole of the same character as the one shown in FIG. 1B.

Figure 6A:
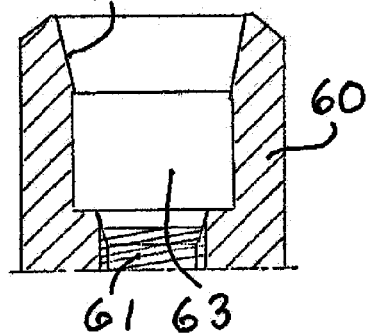
FIG. 6A is a schematic cross-sections of parts comprised in the device according to FIG. 5.
Figure 6B:
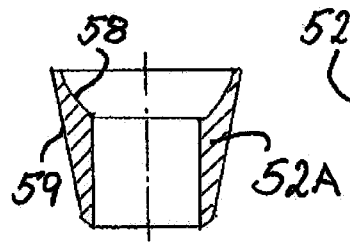
FIG. 6B is a schematic cross-sections of parts comprised in the device according to FIG. 5.
Figure 6C:
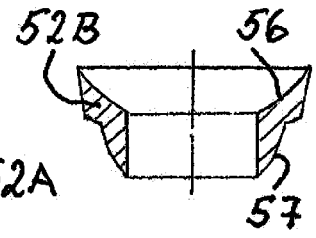
FIG. 6C is a schematic cross-sections of parts comprised in the device according to FIG. 5.

The lower implant cooperating part 52A, also shown in FIG. 6B, and the upper implant cooperating part 52B, also shown in FIG. 6C, are rings or collars, which are movable or rotatable in relation to each other, as will be described, and together form the implant cooperating part 52, corresponding to the implant cooperating part 12 in the FIG. 1 embodiment.

The upper implant cooperating part 52B has a distal concave screw channel part seat 56 with a radius corresponding to the radius of the outer proximal end of the screw channel part 51, i.e. its bottom surface 55, such that the screw channel part 51 may be tilted or angled in relation to the upper implant cooperating part 52B. Also, the upper implant cooperating part 52B has a proximal convex bottom surface 57, preferably with a smaller radius than the concave seat 56.

The lower implant cooperating part 52A has a distal concave upper implant cooperating part seat 58 with a radius corresponding to the radius of the proximal convex bottom surface 57 of the upper implant cooperating part 52B, such that the upper implant cooperating part 52B may be tilted or angled in relation to the lower implant cooperating part 52A.

The bottom surface 57 and the seat 58 may be said to form a first ball joint 57, 58. Likewise, the bottom surface 55 and the seat 56 may be said to form a second ball joint 55, 56.

The lower implant cooperating part 52A generally has an exterior frusto-conical shape with a tapering cylindrical outer peripheral surface 59 with its larger diameter towards its upper end.

A dental implant 60 may have a generally cylindrical shape. Coaxially with its central axis it is provided with an internal thread 61 for a screw member 62. Also coaxially with its central axis the dental implant 60 is provided with a cavity 63 for housing the lower implant cooperating part 52A. Towards its mouth the cavity 63 has a tapering portion 64 with a taper corresponding to the taper of the peripheral surface 59 of the lower implant cooperating part 52A. This tapering portion 64 preferably has the same diameter at its mouth as the maximal diameter of the lower implant cooperating part 52A, so that the latter when inserted into the dental implant cavity 63 lies flush with the upper end of the dental implant 60.

For mounting, the lower implant cooperating part 52A is preferably first placed in the cavity 63 of the dental implant 60 with its tapering peripheral surface 59 in contact with the tapering portion 64 of the dental implant cavity 63. The upper implant cooperating part 52B is then placed with its proximal convex bottom surface 57 in the concave seat 58 of the lower implant cooperating part 52A. Finally, the screw channel directing part 51 is placed in the concave seat 56 of the upper implant cooperating part 50 with its convex outer bottom surface 55.

The screw channel directing part 51 has a long hole in its screw member seat 54, whereas the upper and lower implant cooperating parts 52A, B have central through holes for the screw member 62—inserted through the screw channel directing part 51—to extend through, down into the internal thread 61 of the dental implant 60.

The screw member 62 has a screw member head 65 with a tool grip 66 in its free axial end. The lower side of the screw member head 65 has a convex shape conforming to the concave shape of the screw member seat 54 in the screw channel directing part 51.

When the different members have been moved into appropriate positions for accomplishing a desired position for the screw channel part 51 in relation to the dental implant 60, the screw member 62 may be tightened into its internal thread 61 in the dental implant 60 by means of an appropriate tool 67 inserted into the screw channel part and cooperating with the tool grip 66 of the screw member head 65.

The divided implant cooperating part 52A, B provides an improved freedom to position the screw channel part 51 in relation to the dental implant 60. It will be possible not only to tilt or angle the screw channel part 51 but also to transfer it sideways to a certain extent by tilting the upper implant cooperating part 52B in relation to the lower implant cooperating part 52A. The construction increases the possible tolerances in the superstructure to be fastened to the dental implant.

In a preferred embodiment the radii of the bottom surface 57 of the upper implant cooperating part 52B and the seat 58 of the lower implant cooperating part 52A are smaller than the radii of the seat 56 of the upper implant cooperating part 52B and the bottom surface 55 of the screw channel part 51. This means that the distance between their respective rotation centers is increased for greater versatility.

The screw channel can be placed hidden on the occlusal surface or behind the incical area. It the superstructure is cast, the precision is not always perfect. The construction shown in FIG. 5 can manage deviations up to 5 degrees depending on the size of the screw member.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A screw channel directing device for a dental superstructure, comprising:
  a screw channel part and an implant cooperating part, said screw channel part comprising:
    a distal end and a proximal end, the proximal end constructed to couple with the implant cooperating part; and
    a screw member seat with an elongated screw hole in the proximal end,
  wherein the proximal end of the screw channel part is bowl shaped, such that the inner bottom surface has a concave shape and its outer bottom surface has a convex shape, and
  wherein said implant cooperating part comprises:
    a collar-shaped lower implant cooperating part to be connected to a dental implant, the lower implant cooperating part comprising a distal concave seat, and
    a collar-shaped upper implant cooperating part, said upper implant cooperating part comprising a proximal convex bottom surface with a radius corresponding to the radius of the concave seat of the lower implant cooperating part to form a first ball joint and said upper implant cooperating part having a distal concave seat with a radius corresponding to the radius of the outer bottom surface of the screw channel part to form a second ball joint, wherein the second ball joint has a radius that is different from a radius of the first ball joint,
  wherein the two ball joints are constructed such that the upper implant cooperating part and the screw channel part are capable of being tilted in relation to a central axis of the lower implant cooperating part and the dental implant when a screw member is engaged with the dental implant.

2. The screw channel directing device according to claim 1, wherein the first ball joint has a smaller radius than the second ball joint.

3. The screw channel directing device according to claim 1, wherein the lower implant cooperating part has an exterior frusto-conical shape and fits into a tapering portion of a cavity in the upper end of the dental implant.

4. The screw channel directing device according to claim 3, wherein the dental implant is provided with an internal thread in conjunction with the cavity, the thread being intended for cooperation with a screw member to be inserted through the screw channel part, the upper implant cooperating part, and the lower implant cooperating part.

5. The screw channel directing device according to claim 1, wherein at least the screw channel part is of a plastic material.

6. The screw channel directing device according to claim 1, wherein at least the screw channel part is of metal.

7. The screw channel directing device of claim 1, wherein the elongated hole extends from a central axis toward a perimeter of the screw channel part.

\* \* \* \* \*